US011026652B2

(12) United States Patent
Dorn

(10) Patent No.: US 11,026,652 B2
(45) Date of Patent: Jun. 8, 2021

(54) METHOD AND SYSTEM FOR PROVIDING A DOSE REFERENCE VALUE FOR A PATIENT

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/575,662

(22) Filed: Sep. 19, 2019

(65) Prior Publication Data
US 2020/0100755 A1   Apr. 2, 2020

(30) Foreign Application Priority Data
Sep. 28, 2018  (EP) ..................................... 8197456

(51) Int. Cl.
*A61B 6/03* (2006.01)
*G16H 70/20* (2018.01)
*G16H 40/60* (2018.01)
*A61B 6/00* (2006.01)
*G16H 30/20* (2018.01)

(52) U.S. Cl.
CPC ............ *A61B 6/545* (2013.01); *A61B 6/5294* (2013.01); *A61B 6/544* (2013.01); *G16H 40/60* (2018.01); *G16H 70/20* (2018.01); *A61B 6/03* (2013.01); *G16H 30/20* (2018.01)

(58) Field of Classification Search
None
See application file for complete search history.

(56) References Cited

U.S. PATENT DOCUMENTS

| | | | | |
|---|---|---|---|---|
| 6,901,129 B2 * | 5/2005 | Tachizaki | ............... | A61B 6/583 378/4 |
| 6,954,513 B2 * | 10/2005 | Horiuchi | ................ | A61B 6/542 378/165 |
| 9,275,189 B2 * | 3/2016 | Walker | ................... | A61B 6/545 |
| 9,687,201 B2 * | 6/2017 | Yanagida | ............... | A61B 6/544 |

(Continued)

FOREIGN PATENT DOCUMENTS

JP   2011045709 A   3/2011

OTHER PUBLICATIONS

Alsuwaidi, Jamila Salem et al. "National survey on medical exposure to patients undergoing diagnostic radiology examinations: An initial overview on CT doses at UAE hospitals" Biomedical Engineering (MECBME), 2011 1st Middle East Conference on, IEEE, Feb. 21, 2011, pp. 400-402, // DOI: 10.1109/MECBME.2011. 5752150, ISBN: 978-1-4244-6998-7.

(Continued)

*Primary Examiner* — Thomas R Artman
(74) *Attorney, Agent, or Firm* — Harness, Dickey & Pierce, P.L.C.

(57) ABSTRACT

A computer-implemented method and a system are for providing a dose reference value for a patient. In an embodiment, the method includes: determining a body parameter value for each of at least one body parameter of a patient; determining an adjustment factor based at least on the at least one determined body parameter value of the patient; determining a base dose reference value; and providing the dose reference value for the patient based on the base dose reference value adjusted using the determined adjustment factor.

24 Claims, 2 Drawing Sheets

(56) References Cited

U.S. PATENT DOCUMENTS

| | | | |
|---|---|---|---|
| 2003/0016778 A1 | 1/2003 | Tachizaki et al. | |
| 2004/0131141 A1* | 7/2004 | Horiuchi | A61B 6/542 378/4 |
| 2008/0292055 A1 | 11/2008 | Boone | |
| 2012/0213326 A1 | 8/2012 | Olszewski et al. | |
| 2013/0279644 A1* | 10/2013 | Yanagida | A61B 6/032 378/8 |
| 2015/0100290 A1* | 4/2015 | Falt | A61N 5/1075 703/2 |
| 2016/0196406 A1 | 7/2016 | Falt et al. | |

OTHER PUBLICATIONS

Imagegently "How to Develop CT Protocols for Children" Jan. 1, 2011 (Jan. 1, 2011),Retrieved from the Internet: URL: https://www.imagegently.org/portals/6/procedures/protocols.pdf [retrieved on Jun. 19, 2020].

European Office Action dated Jun. 25, 2020.

LOINC version 2.64 released on Jun. 15, 2018, as is available e.g. from http:\\loinc.org\.

"RadLex Playbook and the LOINC/RSNA Radiology Playbook"; by RSNA; https://www.rsna.org/RadLex_Playbook.aspx; Sep. 18, 2018.

NPL: Extended European Search Report for EP Application Patent No. 18197456.9, dated Mar. 25, 2019 and English translation herewith.

* cited by examiner

METHOD AND SYSTEM FOR PROVIDING A DOSE REFERENCE VALUE FOR A PATIENT

PRIORITY STATEMENT

The present application hereby claims priority under 35 U.S.C. § 119 to European patent application number EP18197456.9 filed Sep. 28, 2018, the entire contents of which are hereby incorporated herein by reference.

FIELD

At least one embodiment of the present invention generally relates to a computer-implemented method, and a system, for providing a dose reference value for a patient. Providing the dose reference value may in particular comprise, or consist of, displaying, storing and/or transmitting the dose reference value.

BACKGROUND

Nowadays, a large number of non-invasive medical imaging techniques are available to better investigate and diagnose the medical status of a patient.

Most non-invasive medical imaging techniques subject the patient to a dose of electromagnetic radiation in individual scans which can therefore be designated as "dose events". Each such individual scan is associated with a corresponding "dose value", which indicates for each dose event in a suitable manner the dose of electromagnetic radiation that has been applied.

For example, the CT dose index (CTDI) is a standardized measure of a radiation dose value output by e.g. a CT scanner which allows comparing radiation output of different devices. $CTDI_w$ (sometimes also written as CTDIw) is the weighted average of dose across a single scan slice. $CTDI_{Vol}$ (sometimes also written as $CTDI_{Vol}$) is obtained by dividing $CTDI_w$ by a pitch factor.

The also commonly used dose length product (DLP) factors in the length of the scan to show an overall dose output, i.e.

$$DLP = CTDI_{Vol} \text{ times scan length.}$$

There is a demand to keep track of dose events and applied dose values in order to enable awareness of the total amount of electromagnetic radiation applied to a patient over a time. Apart from cumulative dose values, it is also of interest to compare individual dose values of a specific dose event to dose reference values in order to determine whether a lower or higher dose event might be warranted or possible, respectively.

It is evident that medical diagnostic tasks are made easier for the physician when there is more, and more detailed and precise, image data of the patient. However, producing more, and more detailed, image data also means subjecting the patient to higher doses of radiation. It is therefore important to have well-defined reference values such as to balance these two opposite aspects.

National agencies as well as institutions have therefore defined dose reference values for body regions with the goal that the dose values of an individual scan of a planned exam will not exceed the reference values except in special circumstances where a physician decides that such measures are warranted by the patient's situation.

In general, dose reference values are often only defined for adults. The body of an adult is, however, vastly different from the body of a child, and even children of different ages have strongly varying body parameter values (such as age, weight, body height and so on). A dose reference value that is well suited for an adult may still be applicable for a seventeen-year-old but may not very well relate to a twelve-year-old and may not relate at all to a toddler or newborn.

Moreover, dose management products supporting bench marking functionality need to map local exam protocols to a standard or ontology such as the "RadLex playbook" (registered trademark), which defines exam protocols for different modalities including, for example, CT. In other words, ontologies such as the RadLex ontology have been introduced in order to standardize data recording formats such that the dose events (and dose values) can be noted and compared even if they stem from different modalities at different tenants using different scanning equipment and so on.

The RadLex playbook has been introduced by the Radiological Society of North America (RSNA) and constitutes a portion of the RadLex ontology (meanwhile also part of the more general LOINC standard). The RadLex playbook aims to provide a standard system for naming radiology procedures, based on the elements, which define an imaging exam such as modality and body part, among others. By providing standard names and codes for radiological studies, the RadLex playbook is intended to facilitate a variety of operation and quality improvement efforts, including radiation dose tracking and image exchange.

Whenever reference is made herein of the RadLex (registered trademark) ontology, it is referred to the current RadLex version 2.5 released in February 2018. However, the concepts described herein may be equally applicable for future versions of the standard. More information about the RadLex playbook can e.g. be obtained at the world wide web URL: https://www.rsna.org/RadLex_Playbook.aspx.

Other projects include e.g. the LOINC-RSNA Radiology Playbook, which is jointly managed by the Regenstrief Institute (publisher of LOINC) and RSNA. This harmonized playbook defines a new information model for describing imaging procedures, and identifies correspondences between RadLex playbook codes and LOINC codes.

Whenever reference is made herein of LOINC (registered trademark) it is referred to the LOINC version 2.64 released on Jun. 15, 2018, as is available e.g. from http:\\loinc.org\. However, the concepts described herein may be equally applicable for future versions of the standard.

Using such a set of introduced standard protocols (e.g. RadLex playbook identifier, RPID, 315), a comparison between different exams (e.g. head exams) from different tenants (e.g. a specific hospital) with different scanner devices (e.g. having a specific device serial number) from different vendors can be accomplished when the individual exam has been mapped to the standard protocol before the comparison starts.

However, there is typically no explicit distinction between different pediatric levels (i.e. different categories of non-adults) and adults. Sometimes, at most exactly two categories (adult and child/non-adult) are taken into account. For many pediatric examinations (for example for very small and/or young children such as toddlers) the reference values are not ideally suited for the task at hand.

The term "adult" may refer to a person having a specific minimum age, which may, however, vary from country to country. For example, adults may be defined to be eighteen years or older, twenty years or older, twenty-one years or older and so on. It is, however, for every jurisdiction and every state clear what the legal definitions for an adult are.

SUMMARY

At least one embodiment of the present invention provides an improved method and/or system for providing dose reference values for patients.

At least one embodiment of the present invention is directed to a computer-implemented method for providing a dose reference value for a patient is provided, comprising:

determining at least one body parameter value of a patient;

determining an adjustment factor based at least on the at least one determined body parameter value of the patient;

determining a base dose reference value; and providing (in particular determining, reading out and/or calculating) the dose reference value for the patient based on the base dose reference value adjusted using the determined adjustment factor.

According to a second embodiment, the invention provides a system for providing a dose reference value for a patient, comprising:

a body parameter determining module, configured to determine a body parameter value for at least one body parameter of a patient;

an adjustment factor determining module, configured to determine an adjustment factor, based at least on the body parameter value for at least one body parameter of the patient determined;

a base dose reference value determining module, configured to determine a base dose reference value; and an output module, configured to provide the dose reference value for the patient based on the base dose reference value adjusted using the adjustment factor determined.

According to a third embodiment, the invention provides a system configured to perform the method according to the first embodiment of the invention.

According to a fourth embodiment of the present invention, a non-transitory computer-readable storage medium is provided that comprises executable program code configured to, when executed (in particular when executed by the system according to the second or third embodiment of the invention), the former method according to an embodiment of the first embodiment.

According to a fifth embodiment of the present invention, a computer program product is provided which comprises executable program code configured to, when executed (in particular when executed by the system according to the second or third embodiment of the invention), perform the method according to an embodiment of the first embodiment of the invention.

According to a sixth embodiment of the present invention, a data stream is provided that comprises, or is configured to generate, executable program code configured to, when executed (in particular when executed by the system according to the second embodiment or the third embodiment of the invention), perform the method according to an embodiment of the first embodiment of the invention.

According to another embodiment, the invention provides a system for providing a dose reference value for a patient, comprising:

a memory storing computer-readable instructions; and one or more processors configured to execute the computer-readable instructions such that the one or more processors are configured to determine a body parameter value for at least one body parameter of a patient;

to determine an adjustment factor, based at least on the body parameter value for at least one body parameter of the patient determined;

to determine a base dose reference value; and to provide the dose reference value for the patient based on the base dose reference value adjusted using the adjustment factor determined.

BRIEF DESCRIPTION OF THE DRAWINGS

The invention will be explained in greater detail with reference to example embodiments depicted in the drawings is appended.

The accompanying drawings are included to provide a further understanding of the present invention and are incorporated in and constitute a part of this specification. The drawings illustrate the embodiments of the present invention and together with the description serve to explain the principles of the invention.

Other embodiments of the present invention and many of the intended advantages of the present invention will be readily appreciated as they become better understood by reference to the following detailed description.

Figure 1:
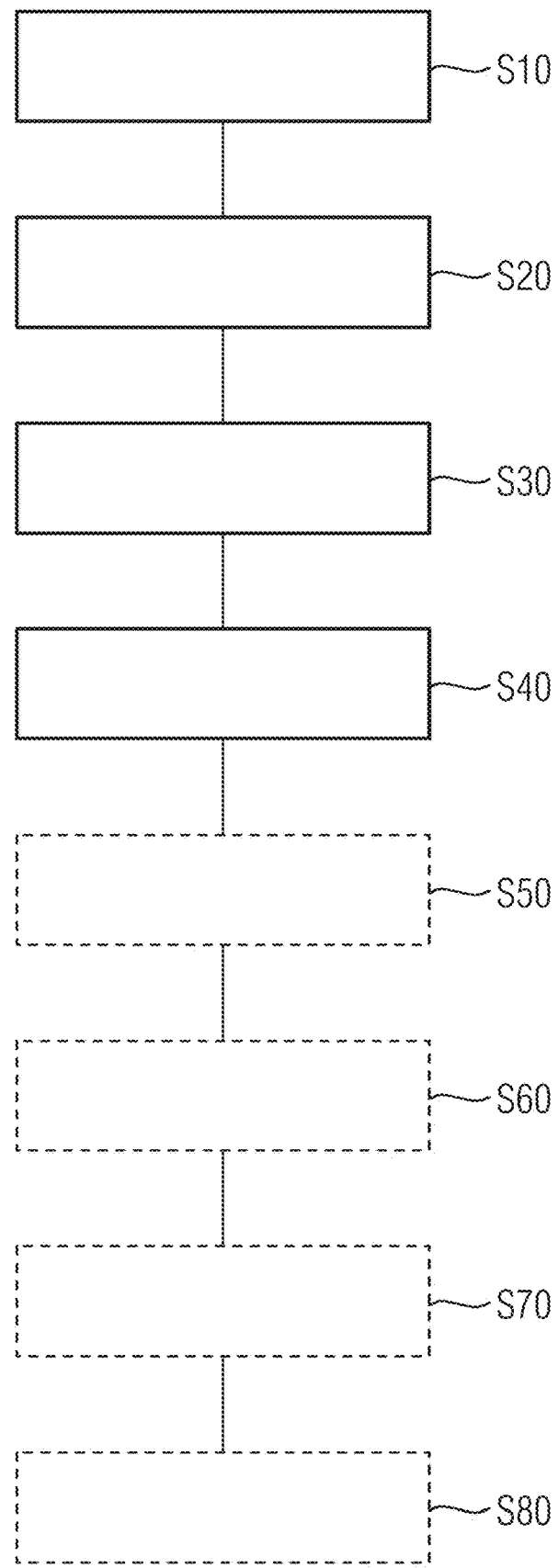
Figure 2:
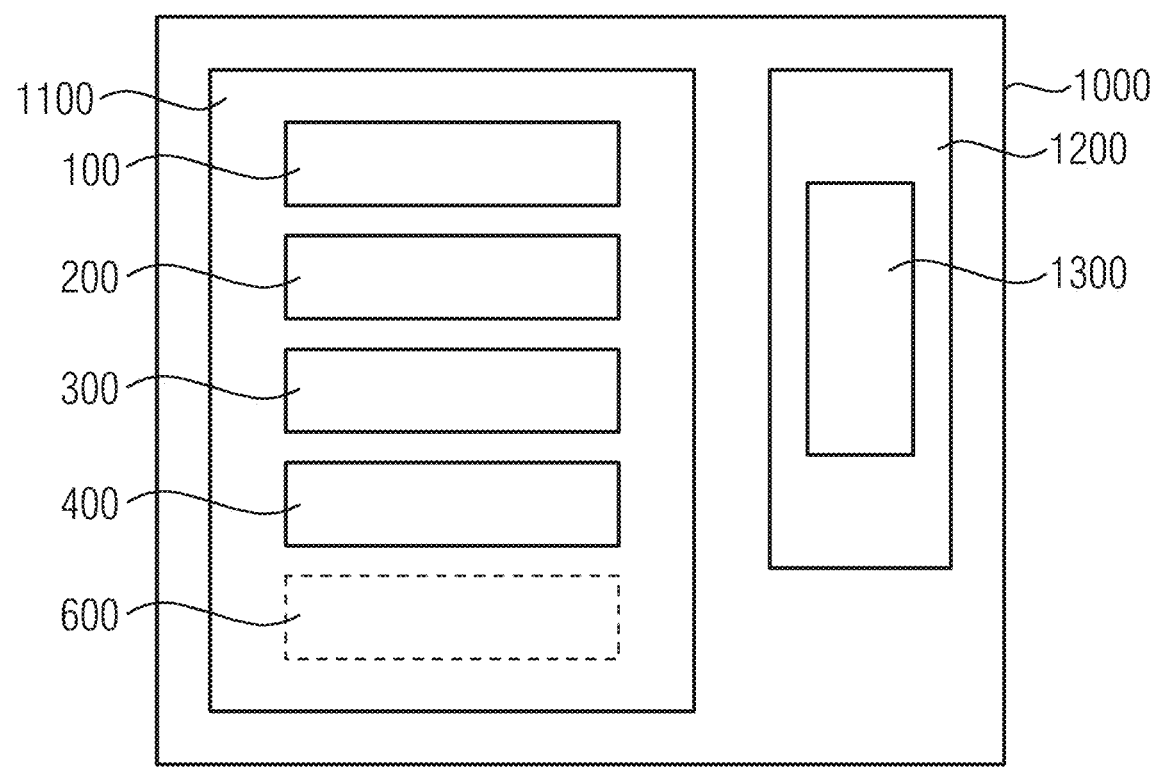

FIG. 1 schematically illustrates a flow diagram for illustrating a computer-implemented method for providing a dose reference value for a patient according to an embodiment of the present invention; and FIG. 2 shows a schematic block diagram illustrating a system for providing a dose reference value for a patient according to the second embodiment of the present invention.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a computer-implemented method for providing a dose reference value for a patient is provided, comprising:

determining at least one body parameter value of a patient;

determining an adjustment factor based at least on the at least one determined body parameter value of the patient;

determining a base dose reference value; and providing (in particular determining, reading out and/or calculating) the dose reference value for the patient based on the base dose reference value adjusted using the determined adjustment factor.

In this way, the base dose reference value preferably acts as a fixed point from which other personalized dose reference value can be calculated. The base dose reference value is preferably a dose reference value determined for adults.

Using the at least one body parameter value of the patient thus allows a more suitable, adjusted dose reference value to be determined for the patient using however a base dose reference value that serves as a general benchmark. The dose reference value for the patient may be provided as a simple product of the adjustment factor and the base dose reference value; however, in some embodiments, the dose reference value may be provided as another type of function of the base dose reference value and of the determined adjustment factor.

The method according to the first embodiment allows a fair comparison of an intended dose value of an exam for a patient with a suitable dose reference value.

According to a second embodiment, the invention provides a system for providing a dose reference value for a patient, comprising:

a body parameter determining module configured to determine a body parameter value for each of at least one body parameter of a patient;

an adjustment factor determining module configured to determine an adjustment factor based at least on the at least one determined body parameter value of the patient;

a base dose reference value determining module configured to determine a base dose reference value; and an output module configured to provide (in particular: determine, read out and/or calculate) the dose reference value for the patient based on the base dose reference value adjusted using the determined adjustment factor, preferably adjusted by multiplying the base dose reference value with the adjustment factor.

The modules of the system according to the second embodiment of the invention may be realized partially or completely in hardware and/or software. The system may comprise a computing device configured to implement the modules of the system as software modules.

The computing device may be realized as any device, or any means, for computing, in particular for executing a software, an App, or an algorithm. For example, the computing device may comprise a central processing unit (CPU) and a memory operatively connected to the CPU. The computing device may also comprise an array of CPUs, an array of graphical processing units (GPUs), at least one application-specific integrated circuit (ASIC), at least one field-programmable gate array (FPGA), and/or any combination of the foregoing. Some, or even all, modules of the system may be implemented by a cloud computing platform.

The system may comprise a graphical user interface, GUI, that is configured to allow a user to continuously interact in a guided way with the system in order to provide the dose reference value for the patient. In particular, the graphical user interface may be configured to receive at least one body parameter value of the patient via a user input.

According to a third embodiment, the invention provides a system configured to perform the method according to the first embodiment of the invention.

According to a fourth embodiment of the present invention, a non-transitory computer-readable storage medium is provided that comprises executable program code configured to, when executed (in particular when executed by the system according to the second or third embodiment of the invention), the former method according to an embodiment of the first embodiment.

The storage medium may be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Laserdisc, Phasewriter (Phasewriter Dual, PD), Compact Disc (CD), Digital Video Disc (DVD), High Definition DVD (HD DVD), Blu-ray Disc (BD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM) or a data carrier/medium.

According to a fifth embodiment of the present invention, a computer program product is provided which comprises executable program code configured to, when executed (in particular when executed by the system according to the second or third embodiment of the invention), perform the method according to an embodiment of the first embodiment of the invention.

According to a sixth embodiment of the present invention, a data stream is provided that comprises, or is configured to generate, executable program code configured to, when executed (in particular when executed by the system according to the second embodiment or the third embodiment of the invention), perform the method according to an embodiment of the first embodiment of the invention.

Further advantageous embodiments, variations and modifications will be presented in the dependent claims and in the description in combination with the figures.

In some advantageous embodiments, the adjustment factor is determined as a function of at least the determined at least one body parameter value, wherein the function is a monotonous function of the at least one body parameter value, preferably a monotonously increasing function of the at least one body parameter value. In variants where there are multiple body parameters set for which body parameter values are to be determined, preferably the adjustment factor is a monotonous function of all of the set body parameters.

Especially preferably the function may be a strictly monotonously increasing function. The function may be defined piece-wise, for example with continuous sections for each of a plurality of predefined categories, or value groups, of the at least one body parameter value. It has been found that most body parameter values such as age, body height, body weight and so on linearly correspond to the capacity of the body to tolerate dose amounts. In other words, the higher the body parameter value is, the higher the dose values tolerable by the body are and, correspondingly, the higher suitable dose reference values should be set.

In some advantageous embodiments, a first body parameter of the at least one body parameter of the patient indicates an age or an age category of the patient, and the adjustment factor is determined based at least on the indicated age or age category of the patient. Preferably, the adjustment factor is expressed or expressible by a monotonously increasing function of the indicated age or age category.

In some advantageous embodiments, a plurality of age categories is defined, including at least two different age categories for non-adults, wherein one age category of the plurality of age categories is automatically selected based on the determined first body parameter, wherein the adjustment factor is determined based at least on the automatically selected age category.

Preferably, at least three different age categories for non-adults are defined, for example four, five or six age categories for non-adults. The age categories are preferably defined such that they do not overlap. In this way, each patient clearly falls under one (and only one) of the defined age categories. Higher numbers of age categories results in a more precisely determinable dose reference value but on the other hand may complicate comparisons over different age categories. The system and method may also be implemented such that the number of different age categories is variable. In that case, the adjustment factors may be automatically adjusted.

In some advantageous embodiments, one specific age category of the plurality of defined age categories is designated as a default age category that is used as a default when the one age category of the plurality of age categories is automatically selected based on the determined first body parameter value.

For example, the first body parameter may refer to an age or age category of the patient, and a first body parameter value that is automatically determined may indicate that the age or age category of the patient is unknown. As a result, the default age category is then selected and the adjustment factor is determined based on the selected default age category. For example, an age category into which 6-year-olds, 7-year-olds, 8-year-olds, 9-year-olds and/or 10-year-olds are grouped may be defined to be the default age category.

In some advantageous embodiments, a second body parameter of the at least one body parameter of the patient indicates a body weight or a body weight category of the patient, and the adjustment factor is determined based at least on the indicated body weight or body weight category of the patient according to the body parameter value for the second body parameter.

It has been found that also the body weight, and/or a corresponding body weight category, of the patient relate well to a tolerance of the patient for dose values, i.e., the more body weight a patient has, the more tolerant the patient's body usually is of higher dose values, and the higher the corresponding dose reference value for that patient can be set. Preferably, the adjustment factor is a monotonously increasing function of the body weight or body weight category, of the patient (i.e. of the second body parameter).

In some advantageous embodiments, a third body parameter of the at least one body parameter of the patient indicates a body height or body height category of the patient, and the adjustment factor is determined based at least on the indicated body height or body height category of the patient according to the body value parameter for the third body parameter.

It has been found that also the body height, and/or a corresponding body height category, of the patient relate well to a tolerance of the patient for dose values, i.e., the taller a patient is, the more tolerant the patient's body usually is of higher dose values, and the higher the corresponding dose reference value for that patient can be set. Preferably, the adjustment factor is a monotonously increasing function of the body height or body height category, of the patient (i.e. of the third body parameter).

In some advantageous embodiments, the base dose reference value is determined by retrieving it from a database. For example, the base dose reference value may be equal to a dose reference value provided and/or calculated for an adult. This is often a suitable choice as most countries and agencies provide dose reference values for adults, even if many of them do not provide explicit dose reference values for non-adults (let alone for multiple categories of non-adults).

The base dose reference value may be, or be based on, an average, an extrapolation, and/or an interpolation from different candidate dose reference values provided by different national agencies and/or national institutions such as health departments, health ministries, health research facilities, research clinics, medical chairs of universities, polls among experts and/or the like.

Providing and storing the base dose reference value allows also to adapt the present method easily when new scientific findings necessitate a change of the base dose reference value. In that case, the base dose reference value stored in the database may simply be exchanged and the remaining method may (including, for example, how the adjustment factor is determined) continue without any additional changes. This is a major simplification.

In some advantageous embodiments, the base dose reference value is determined by at least the following:

retrieving, from a database, at least two candidate dose reference values (for example by a national institution or a national agency); and calculating, from the retrieved at least two candidate dose reference values, the base dose reference value by interpolation, extrapolation and/or averaging.

Similarly, the adjustment factor itself may be determined by comparing available adapted dose reference values for specific body parameter categories from different national agencies and/or institutions.

For example, health departments of some countries may provide dose reference values for children from zero to eight years and for children from nine to seventeen years, respectively. Other health departments of other nations may provide reference values for children from zero to three years, from four to six years, from seven to ten years, and from eleven to seventeen years, respectively, designating people of age 18 or older as adults.

In each case, the dose reference value for the non-adult categories may be compared to the dose reference value provided by the same health department for an adult. From that, percentages of the dose reference values for the non-adult categories may be calculated as compared to the dose reference value for adults. The adjustment factor may then be determined, for a specific non-adult age category, based on a interpolation, extrapolation and/or averaging of the different fractions of the adult dose reference value provided by the different sources.

Averaging may comprise forming a mean, a medium, or other averaging techniques. In the above example, the dose reference value for adults (adult dose reference value) was used as point of comparison. This is especially preferable in embodiments of the present method in which the base dose reference value is (set to be) the same as the adult dose reference value.

In some advantageous embodiments, the method comprises evaluating a report file of an exam previously performed on the patient and/or a data file for an exam intended for the patient in order to extract from the report file and/or data file, respectively, a piece of information that allows to determine a body parameter value for at least one of the at least one body parameters of the patient.

In case the piece of information has been extracted, the body parameter value for the at least one body parameter is determined based on the extracted piece of information. In case no piece of information has been extracted, the body parameter value for the at least one body parameter may be set to a default value, for example as has been described in the foregoing with respect to the default age category. For example, results of medical exams may be stored in a file according to the DICOM standard.

DICOM (registered trademark) refers to "Digital Imaging and Communications in Medicine" and is an international standard to transmit, store, retrieve, print, process and display medical imaging information. When reference is made of DICOM herein, it is referred to the DICOM version DICOM PS 3.1 2018c. However, the concepts described herein may be equally applicable for future versions of that standard.

Such DICOM files usually comprise a header, which generally includes body parameter values for at least one body parameter of the patient, for example, the patient's age, body weight, body height, gender and/or the like. Said information may then be automatically extracted so that, using the method according to the first embodiment of the present invention, the corresponding patient can be provided with an improved dose reference value.

In some advantageous embodiments, the method comprises receiving a modality information signal, which indicates a specific modality, for example a modality that has been used on the patient or which is intended to be used on the patient. The adjustment factor may be determined also based on the received modality information signal, i.e., based on the specific modality indicated by the received modality information signal.

The term "modality", as used herein, refers to a type of the source of medical information about a patient, in particular to a type of medical imaging device, such as a computer tomography (CT) scan, a mammography scan, a molecular imaging (nuclear medicine, NM or positron tomography, PT) scan, X-Ray scan and so on. Of course, additional modalities exist such as genetic tests, lab results, questionnaires, blood work and so on, but the present invention is focused specifically on medical imaging modalities, which are associated with dose events and dose values.

In some advantageous embodiments the method further comprises: receiving a dose value of, or for, the patient;

comparing the received dose value to the provided dose reference value; and outputting a comparison signal when the received dose value is higher than the provided dose reference value.

In this way, a physician or medical technician can be immediately and automatically notified when an intended dose value is too high with respect to the provided dose reference value for that individual patient. In this way, a more precise comparison of a dose value for a patient and the specific dose reference value for such specific patient is enabled.

At least some embodiments of the present invention thus allow generating reliable dose alerts which take into account different age categories for pediatric levels and adapt defined dose reference values automatically such that dose alerts are created more precisely.

In some advantageous embodiments, the method further comprises: graphically displaying the provided dose reference value to a user together with any or any combination, of the following:
  a statistically determined maximum value for a dose value for the patient;
  a value of 75% of the statistically determined maximum value for a dose value for the patient;
  a statistically determined average value for the dose value for the patient;
  a statistically determined medium value for the dose value for the patient;
  a value of 50% of the statistically determined maximum value for a dose value for the patient;
  a value of 25% of the statistically determined maximum value for a dose value for the patient;
  a statistically determined minimum value for the dose value for the patient.

The above-mentioned statistically determined quantities may be determined from a large number of recorded dose values for a large number of patients and/or from a number of reference values provided by different national agencies, institutions, and so on as described in the foregoing.

By displaying the provided dose reference value according to the present method together with any or all of said other values, which may also act in a sense as references, a physician or medical technician can gauge much better whether a certain intended dose value of a dose event for a patient is adequate, tolerable and suitable.

The provided dose reference value according to the present method has the advantage that it has been determined based on the at least one body parameter value for a specific patient.

For example, when the patient in question is a newborn child of five days, the usual statistically determined reference quantities will almost certainly be much higher than the dose reference value provided according to the present method. The discrepancy between the displayed dose reference value according to the present method and the other reference quantities may even prompt the physician or medical technician to take other considerations into account, which may lead to a reduced (or in some instances, increased) dose value of a dose event intended for the patient.

Although it has been described that the provided dose reference value may be compared to a dose value of an intended dose event for the patient, the provided dose reference value may also be used to compare an already applied dose value for the patient to said dose reference value in order to gauge the patient's further tolerance for additional dose values.

In some especially advantageous embodiments, the dose reference value is a body-region-specific dose reference value. Recently, an increasing number of medical imaging exams relate to specific body regions only, and different body regions often have quite different tolerance for different dose values. In general, larger body regions have a higher tolerance for higher dose values than comparatively smaller body regions. By providing a body-region-specific dose reference value, it is ensured that the provided dose reference value is not only suited for a specific patient, but also for a specific body region of the patient that is to be examined. In this way, an even more meaningful comparison between the dose reference value and a dose value of an intended exam on a patient, as well as improved benchmarking, is enabled.

In some advantageous embodiments, the method may further comprise the optional step of controlling a medical imaging device (e.g. an x-ray device and/or a computer tomography scanner) to change (or: adapt) one of the parameters of said medical imaging device based on the dose reference value, and optionally also the step of producing an image by the medical imaging device using said changed (or: adapted) parameter.

Although various advantageous options, variants and embodiments have been described in the foregoing with respect to the method according to the first embodiment of the present invention, it should be understood that the same options, variants and embodiments also equally apply to the system according to the second embodiment.

FIG. 1 schematically illustrates a flow diagram for illustrating a computer-implemented method for providing a dose reference value for a patient according to an embodiment of the present invention.

In a step S100, a body parameter value for each of at least one body parameter of a patient is determined. In different embodiments of the method, different body parameters and/or different numbers of body parameters may be set. The number and type of body parameters for which body parameter values are to be determined may be fixed, or a user may decide, e.g. by making the appropriate selections in a graphical user interface, GUI, to select specific body parameters. Then, for the selected body parameters (and only for those) body parameter values may be determined.

In some variants, it may be required to determine a body parameter value for each of the set body parameters. In other variants, which are preferred, default values are provided which are used for body parameter values which have been selected (either as part of a fixed selection for a specific embodiment or deliberately by a user) but for which no corresponding body parameter value is available (or was not able to be determined).

As has been described in the foregoing, different body parameter of the patient may be selected to be determined by the present method, for example, an age or age category, a body weight or body weight category, a body height or body height category, a sex (male, female, etc.), a medical condition (some medical conditions may influence a patient's tolerance for higher dose values) and so on.

In the following, the method will be described using the example of a age category of the patient being determined as a body parameter of the patient and the ensuing processing. It should be understood, however, that the same steps, variants and options as described in the following with respect to the age category of the patient may also be equally applied to the other mentioned body parameters.

Since one aim of the present invention is to provide a dose reference value that is adapted to the patient as much as possible, it is preferred that body parameter values for a plurality of body parameters are determined for the patient, and it is especially preferred that the plurality of body parameters for which body parameter values are determined comprises an age category, a body weight category and a body height category. It should be understood that in some variants, in each case instead of the category also the exact value of the quantity in question may be determined.

In other words, determining a body parameter value for an age category of the patient (e.g. six to ten years) may be replaced by determining a body parameter value for an age of the patient (e.g. seven years). The same analogously applies for body height and body height category as well as for a body weight and body weight category, respectively.

Determining one particular body parameter value may comprise receiving a user input indicating said body parameter value. For example, the user may, in a graphical user interface, GUI, select an age category of the patient from a graphical manual, such as dropdown manual. The GUI may be configured to display, as a result, only information (for example a box plot) related to the selected body parameter value, e.g. age category.

Additionally or alternatively, in the same embodiment or in other embodiments a report file of an exam previously performed on the patient and/or a data file for an exam intended for the patient is evaluated with the goal to extract from the report file or data file, respectively, a piece of information that allows to determine a body parameter value for at least one of the at least one body parameters of the patient. In particular, a DICOM file may be evaluated in this way.

In a step S200, an adjustment factor based at least on the at least one determined body parameter value of the patient is determined. For example, the adjustment factor may be determined by being read out from a table, which associates age categories of patients (or the body parameter values, analogously) with adjustment factors or with individual factors of the adjustment factor.

For example, in case where body parameter values for each of three body parameters are determined, each body parameter value might contribute an individual factor to the adjustment factor, and the overall adjustment factor may be determined as a function of the individual adjustment factors, preferably as a product of the individual adjustment factors.

An example table is given as follows:

For example, six age categories (second column) may be defined as shown in the following Table 1, and the corresponding adjustment factors (third column) shown in the table are provided as multiplication factors for the determined base dose reference value:

TABLE 1 age categories and corresponding adjustment factors

| age category number | patient age category | adjustment factor in percent of base reference value |
|---|---|---|
| 1 | New born (0-10 days) | 30 |
| 2 | 0-1 years | 40 |
| 3 | 1-5 years | 50 |
| 4 | 6-10 years | 70 |
| 5 | 11-15 years | 90 |
| 6 | 16-18 years and adults | 100 |

In other words, 16-year-olds and older, including adults, have an adjustment factor of 100%, or of 1 in the above example table.

One of the age group categories may comprise a part of a children age group (in the above example 16-18 years) as well as all of the adults.

In other embodiments, the adult age category may be completely separate from any child age categories. It should be noted that in the above example the age of eighteen has been determined to be the age defining an adult; in jurisdictions where the age of adulthood is different, the example may be adapted accordingly.

In the above example, when the only body parameter for which a body parameter value was determined was the age category, the base dose reference value was equal to the provided dose reference value for patients in the age category number 6, i.e. for children 16 to 18 years and for adults. This is simply one possible option.

In some embodiments, the adjustment factor may be designed such that no provided dose reference value is exactly equal to the base dose reference value. As is also evident from the above example, some of the age categories may be roughly of the same duration (for example, age categories numbers 3 to 5 each comprise four years) may have different durations (for example, age categories 1, 2 and 3 each have different duration), or the plurality of defined age categories may have a number of age categories with the same duration and a number of age categories with different durations.

Similar tables as Table 1 above may also be provided for other body parameter categories such as a body weight category and a body height category, which may yield corresponding individual adjustment factors as in the third column of Table 1 above. Then, the overall adjustment factor may be determined as a product of the individual adjustment factors provided by the tables in the line that corresponds to the respective determined body parameter value for the patient.

The individual adjustment factors may also be stored in a relational database such that a selection for a body parameter value in one of the body parameters may affect the selection of a body parameter value in another one of the body parameters, or may affect the number and/or type of body parameter itself.

For example, choosing one specific age category (as a body parameter value for the "age category" body parameter) may result in the GUI prompting the user to input a body parameter value for a second body parameter (e.g. body weight), whereas choosing another specific age category may result in the GUI displaying the calculated dose reference value.

For example, for an adult (body parameter value number 6 in Table 1), the body weight of the patient may be important as adults often have widely varying body weight which impacts their tolerance for dose amounts. In that case, the user may be prompted to input a body weight of the patient, or a body weight of the patient may be automatically read out from a report and/or data file, or a default body weight value may be used.

On the other hand, newborn children (body parameter value 1 in Table 1) will usually have roughly the same weight and/or consideration other than weight (e.g. certain organs still developing rapidly) may be more important than weight. In that case, determining a body parameter value for the body weight can be omitted, or may be replaced by determining another body parameter value more relevant for newborns (e.g. sex).

Moreover, a modality information signal may be received, which indicates a specific modality. For example, the graphical user interface, GUI, may provide the user with the option to indicate, or select (e.g. from a dropdown menu) a specific modality. The adjustment factor may then be determined also based on the received modality information signal, in particular based on the specific modality indicated by the modality information signal.

In some embodiments, each modality that can be specified by the modality information signal is associated with a corresponding individual adjustment factor, which may then be used to form the overall adjustment factor as described in the foregoing, for example, by calculating a product of all of the individual adjustment factors.

In cases where a body parameter value for a specific body parameter has not been input by a user and/or has not been automatically retrieved from an existing file (such as a report file or a data file), a default value preset and stored in a database may be used by the method for determining the corresponding body parameter value. In the case of the above-described embodiment using age category of the patient in connection with Table 1, for example the fourth age category (six to ten years) may be used as a default age category for cases where the age of the patient is not currently known.

Since in particular the bodies of non-adults rapidly change their body parameter values, it is preferred that at least two different age categories for non-adults are provided for the method according to FIG. 1 to choose from when determining the age category of the patient as one of the body parameter values. A definition of four or more age categories is even more preferred, in particular the definition of the six age categories according to Table 1.

In a step S300, a base dose reference value is determined. The base dose reference value may be retrieved from a database or may be calculated from at least two candidate dose reference values by interpolation, extrapolation and/or averaging. The candidate dose reference values may be received or retrieved from a database (e.g. an internet-based database, in particular stored in a cloud data storage) may have originally been provided by national institutions and agencies.

As has been described in the foregoing, the base dose reference value may be, or be based on, an average, an extrapolation, and/or an interpolation from different candidate dose reference values provided by different national agencies and/or national institutions such as health departments, health ministries, health research facilities, research clinics, medical chairs of universities, polls among experts and/or the like.

Advantageously, the dose reference value is a body-region-specific dose reference value. For example, the graphical user interface, GUI, may prompt the user to input a body region of an intended dose event, and the base dose reference value determined in step S300 may be based on that user input.

Dose reference values for a specific body region (body-region-specific dose reference values) may be directly provided for said body region. In particular, the body-region-specific base dose reference value may be, or be based on, an average, an extrapolation, and/or an interpolation from different body-region-specific candidate dose reference values provided by different national agencies and/or national institutions such as health departments, health ministries, health research facilities, research clinics, medical chairs of universities, polls among experts and/or the like.

In some embodiments, at least one of the adjustment factors may be determined in step S200 depending on the specific body region. For example, it may be noticed that a certain body region grows with varying speed in different age categories during the development of a person from child to adult. The adjustment factor may then be determined not only based on the age category but also based on the specific body region. For body regions that on average grow faster during certain age categories, the adjustment factor may increase faster within those age categories than for body regions that on average grow comparatively slower in the same age categories.

Alternatively or additionally, body-region-specific dose reference values for some body regions may be provided by interpolation and/or extrapolation from other adjustment factors provided for other body regions, in particular adjacent or overlapping body regions. In that way, even for body regions in for which no candidate dose reference values exist, body-region-specific dose reference values can be accurately provided.

In a step S400, the dose reference value for the patient is provided (determined, read out and/or calculated) based on the base dose reference value adjusted using the determined adjustment factor. The providing S400 of the dose reference value may further comprise displaying, storing and/or transmitting of the dose reference value.

As has been described, the dose reference value may be calculated as a function of the determined adjustment factor (which itself may be calculated as an overall adjustment factor from one or more individual adjustment factors, preferably as a product) and of the base dose reference value, preferably as a product of these two quantities.

As has been described in the foregoing, the dose reference value is advantageously a body-region-specific dose reference value by virtue of the adjustment factor being body-region-specific and/or by virtue of the base dose reference value being body-region-specific.

In an optional step S500, the provided dose reference value is graphically displayed to a user, preferably together with any or any combination, of the following:
- a statistically determined maximum value for a dose value for the patient;
- a value of 75% of the statistically determined maximum value for a dose value for the patient;
- a statistically determined average value for the dose value for the patient;
- a statistically determined median value for the dose value for the patient;
- a value of 50% of the statistically determined maximum value for a dose value for the patient;
- a value of 25% of the statistically determined maximum value for a dose value for the patient;
- a statistically determined minimum value for the dose value for the patient.

This provides a user with an excellent and immediate grasp of all the relevant considerations and comparisons for an intended, or previously performed, dose event.

The method may further comprise the optional steps of:
receiving S600 a dose value of or for the patient (e.g. indicating a dose value of a dose event currently planned or considered for the patient);
comparing S700 the received dose value to the provided dose reference value for that patient; and
outputting S800 a comparison signal (e.g. a warning signal or alert) when the received dose value is higher than the provided dose reference value.

The comparison signal, or alert, may be output graphically, acoustically and/or haptically to a user. The comparison signal may also be configured as a control signal, for example a control signal for controlling a medical imaging device. In some embodiments, the control signal may prevent the medical imaging device from being set such that the applied dose amount would exceed the provided dose reference value, or may prompt a user (e.g. a physician) to confirm that the intended dose event should be carried out regardless.

The method may further comprise the optional step of controlling a medical imaging device (e.g. an x-ray device and/or a computer tomography scanner) to change (or: adapt) one of the parameters of said medical imaging device based on the dose reference value, and optionally also the step of producing an image by the medical imaging device using said changed (or: adapted) parameter.

FIG. 2 shows a schematic block diagram illustrating a system 100 for providing a dose reference value for a patient according to the second embodiment of the present invention. The system 100 is preferably configured such as to perform the method according to the first embodiment of the present invention, in particular such as to perform the method as described with respect to FIG. 1. Thus, the system 100 illustrated by FIG. 2 may in particular be adapted or modified according to any of the options, variants and modifications described herein with respect to the method according to the first embodiment, in particular the method of FIG. 1.

The system 1000 comprises a body parameter determining module 100 configured to determine a body parameter value for each of at least one body parameter value of a patient, in particular as has been described in the foregoing with respect to step S100. The body parameter determining module 100 may be implemented by hardware and/or by software.

The system 1000 further comprises an adjustment factor determining module 200 configured to determine an adjustment factor based at least on the at least one determined body parameter value of the patient, in particular as has been described in the foregoing with respect to step S200.

The system 1000 also comprises a base dose reference value determining module 300 configured to determine a base dose reference value, in particular as has been described in the foregoing with respect to step S300.

The system 1000 further comprises an output module 400 configured to provide the dose reference value for the patient based on the base dose reference value adjusted using the determined adjustment factor, in particular as has been described in the foregoing with respect to step S400.

Preferably, the system 1000 comprises a computing device 1100. The computing device 1100 may be configured to perform the method according to the first embodiment of the invention, in particular according to the embodiment of FIG. 1. In other words, the computing device 1100 may be configured to perform any or all of the steps S100 to S800 as described above. The computing device 1100 may be realized in hardware, and/or in software.

In particular, the computing device 1100 may be configured to implement the body parameter determining module 100, the adjustment factor determining module 200, the base dose reference value determining module 300 and/or the output module 400. More preferably, the computing device 1100 is at least partially, or completely, implemented by a cloud computing platform.

The system 1000 may further comprise a display device 1200 configured to implement a graphical user interface, GUI, 1300 for graphically displaying information to the user and for receiving at least one user input, for example as has been described in the foregoing. In particular, the display device 1200 may configure the GUI 1300 for receiving at least one body parameter value for at least one body parameter, for receiving a modality signal, for receiving a body region signal indicating a body region for which the dose reference value is to be provided and/or the like.

In particular, the GUI 1300 may be configured to graphically display the provided dose reference value to a user, in particular as has been described in the foregoing with respect to the step S500.

The display device 1200 may be operatively coupled to the computing device 1100. For example, the display device 1200 may be integrated into a local device (such as a desktop PC or a terminal) that is operatively connected or connectable to a cloud computing platform acting as computing device 1100.

Accordingly, the provided dose reference value may be advantageously displayed by the GUI 1300 together with any or any combination, of the following:
- a statistically determined maximum value for a dose value for the patient;
- a value of 75% of the statistically determined maximum value for a dose value for the patient;
- a statistically determined average value for the dose value for the patient;
- a statistically determined median value for the dose value for the patient;
- a value of 50% of the statistically determined maximum value for a dose value for the patient;
- a value of 25% of the statistically determined maximum value for a dose value for the patient;
- a statistically determined minimum value for the dose value for the patient.

The computing device 1100 may further be configured to implement a dose alert module 600 configured to compare a dose value received via the GUI 1300 in connection with a patient (e.g. a dose value of a dose event currently planned or considered for that patient) with the provided dose reference value for that patient. The dose alert module 600 may then control the GUI 1300 to output a comparison signal, e.g. a warning signal or an alert, when the received dose value is higher than the provided dose reference value. The dose alert module 600 may also implement other steps as has been described in the foregoing, e.g. outputting a control signal for controlling a medical imaging device.

The embodiments have been chosen and described in order to best explain the principles of the invention and its practical applications, to thereby enable others skilled in the art to best utilize the invention and various embodiments with various modifications as are suited to the particular use contemplated.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing a dose reference value representing a dose to be received by a patient, comprising:
   - determining a body parameter value for at least one body parameter of a patient;
   - determining an adjustment factor representing an amount by which to adjust a final deliverable dose to be received by a patient based at least on the body parameter value determined, for the at least one body parameter of the patient;
   - determining a base dose reference value; and
   - providing an adjusted dose reference value for the patient based on the base dose reference value adjusted using the adjustment factor determined.

2. The method of claim 1, wherein the determining of the adjustment factor includes determining the adjustment factor as a monotonously increasing function of at least the body parameter value determined, for the at least one body parameter of the patient.

3. The method of claim 2, wherein the at least one body parameter of the patient includes a first body parameter, indicating an age or age category of the patient, and wherein the determining of the adjustment factor includes determining the adjustment factor based at least on the age or age category of the patient indicated according to the body parameter value determined for the first body parameter.

4. The method of claim 3, wherein the at least one body parameter of the patient includes a plurality of age categories, including at least two different age categories for non-adults, wherein one age category of the plurality of age categories is automatically selected based on the body parameter value for the first body parameter, and wherein the adjustment factor is determined based at least on the one age category automatically selected.

5. The method according to claim 4, wherein upon one age category of the plurality of age categories being automatically selected based on the body parameter value for the first body parameter, the one specific age category of the plurality of age categories is designated as a default age category that is used as a default.

6. The method of claim 1, wherein the at least one body parameter of the patient includes a first body parameter, indicating an age or age category of the patient, and wherein the determining of the adjustment factor includes determining the adjustment factor based at least on the age or age category of the patient indicated according to the body parameter value determined for the first body parameter.

7. The method of claim 6, wherein the at least one body parameter of the patient includes a plurality of age categories, including at least two different age categories for non-adults, wherein one age category of the plurality of age categories is automatically selected based on the body parameter value for the first body parameter, and wherein the adjustment factor is determined based at least on the one age category automatically selected.

8. The method according to claim 7, wherein upon one age category of the plurality of age categories being automatically selected based on the body parameter value for the first body parameter, the one specific age category of the plurality of age categories is designated as a default age category that is used as a default.

9. The method of claim 7, wherein the at least one body parameter of the patient includes a second body parameter indicating a body weight or body weight category of the patient, and wherein the determining of the adjustment factor includes determining the adjustment factor based at least on an indicated body weight or body weight category of the patient according to the body value parameter for the second body parameter.

10. The method of claim 7, wherein the at least one body parameter of the patient includes a third body parameter indicating a body height or body height category of the patient, and wherein the determining of the adjustment factor includes determining the adjustment factor based at least on the indicated body height or body height category of the patient according to the body value parameter for the third body parameter.

11. The method of claim 1, wherein the at least one body parameter of the patient includes a second body parameter indicating a body weight or body weight category of the patient, and wherein the determining of the adjustment factor includes determining the adjustment factor based at least on an indicated body weight or body weight category of the patient according to the body value parameter for the second body parameter.

12. The method of claim 11, wherein the at least one body parameter of the patient includes a third body parameter indicating a body height or body height category of the patient, and wherein the determining of the adjustment factor includes determining the adjustment factor based at least on the indicated body height or body height category of the patient according to the body value parameter for the third body parameter.

13. The method of claim 1, wherein the at least one body parameter of the patient includes a third body parameter indicating a body height or body height category of the patient, and wherein the determining of the adjustment factor includes determining the adjustment factor based at least on the indicated body height or body height category of the patient according to the body value parameter for the third body parameter.

14. The method of claim 1, wherein the determining of the base dose reference value includes:
retrieving, from a database, at least two candidate dose reference values; and
calculating, from the at least two candidate dose reference values retrieved, the base dose reference value by at least one of interpolation, extrapolation and averaging.

15. The method of claim 1, further comprising:
evaluating at least one of a report file of an exam previously performed on the patient and a data file for an exam intended for the patient in order to extract from the report file or data file, respectively, a piece of information that allows the determining the body parameter value for one of the at least one body parameters of the patient;
wherein, upon the piece of information being extracted, the body parameter value for the one of the at least one body parameter is determined based on the piece of information extracted.

16. The method of claim 1, further comprising:
receiving a modality information signal indicating a specific modality; and
wherein the determining of the adjustment factor includes determining the adjustment factor based on the received modality information signal.

17. The method of claim 1, further comprising:
receiving a dose value of the patient or receiving a dose value for the patient;
comparing the dose value received to the dose reference value provided; and
outputting a comparison signal upon the dose value received being relatively higher than the dose reference value provided.

18. The method of claim 1, comprising:
graphically displaying the dose reference value provided to a user, together with at least one of:
a statistically determined maximum value for a dose value for the patient;
a value of 75% of the statistically determined maximum value for a dose value for the patient;
a statistically determined average value for the dose value for the patient;
a statistically determined median value for the dose value for the patient;
a value of 50% of the statistically determined maximum value for a dose value for the patient;
a value of 25% of the statistically determined maximum value for a dose value for the patient; and
a statistically determined minimum value for the dose value for the patient.

19. The method of claim 1, wherein the dose reference value is a body-region-specific dose reference value.

20. A non-transitory computer readable medium storing executable program code configured to, when executed by a computer, perform the method of claim 1.

21. A system for providing a dose reference value representing a dose to be received by a patient, comprising:
- a body parameter determining module, configured to determine a body parameter value for at least one body parameter of a patient;
- an adjustment factor determining module, configured to determine an adjustment factor representing an amount by which to adjust a final deliverable dose to be received by a patient, based at least on the body parameter value for at least one body parameter of the patient determined;
- a base dose reference value determining module, configured to determine a base dose reference value; and
- an output module, configured to provide an adjusted dose reference value for the patient based on the base dose reference value adjusted using the adjustment factor determined.

22. The system of claim 21, wherein the adjustment factor is determined as a monotonously increasing function of at least the body parameter value determined, for the at least one body parameter of the patient.

23. A system for providing a dose reference value representing a dose to be received by a patient, comprising:
- a memory storing computer-readable instructions; and
- one or more processors configured to execute the computer-readable instructions such that the one or more processors are configured
  - to determine a body parameter value for at least one body parameter of a patient;
  - to determine an adjustment factor representing an amount by which to adjust a final deliverable dose to be received by a patient, based at least on the body parameter value for at least one body parameter of the patient determined;
  - to determine a base dose reference value; and
  - to provide an adjusted dose reference value for the patient based on the base dose reference value adjusted using the adjustment factor determined.

24. The system of claim 23, wherein the adjustment factor is determined as a monotonously increasing function of at least the body parameter value determined, for the at least one body parameter of the patient.

* * * * *

UNITED STATES PATENT AND TRADEMARK OFFICE
CERTIFICATE OF CORRECTION

PATENT NO. : 11,026,652 B2  
APPLICATION NO. : 16/575662  
DATED : June 8, 2021  
INVENTOR(S) : Karlheinz Dorn Page 1 of 1

It is certified that error appears in the above-identified patent and that said Letters Patent is hereby corrected as shown below:

On the Title Page

(30) Foreign Application Priority Data should read as:  
Sep. 28, 2018 (EP).....18197456.9

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*